United States Patent [19]

Poshemansky et al.

[11] Patent Number: 4,766,760
[45] Date of Patent: Aug. 30, 1988

[54] METHOD OF CHROMATOGRAPHIC ANALYSIS OF A MIXTURE OF LIQUID SUBSTANCES AND A GAS CHROMATOGRAPH FOR CARRYING OUT THE METHOD

[75] Inventors: Vladimir M. Poshemansky; Eduard P. Skornyakov; Vitaly P. Chizhkov, all of Moscow, U.S.S.R.

[73] Assignee: Vsesojuzny Nauchno-issledovatelsky i Konstruktorsky istitute Khromatografii, Moscow, U.S.S.R.

[21] Appl. No.: 116,454

[22] Filed: Nov. 3, 1987

[51] Int. Cl.[4] ............................................. G01N 30/38
[52] U.S. Cl. .................................................. 73/23.1
[58] Field of Search ................ 73/23.1, 863.11; 55/67, 55/386; 422/89

[56]    References Cited
U.S. PATENT DOCUMENTS

| 3,798,973 | 3/1974 | Estey | 73/23.1 X |
| 4,269,608 | 5/1981 | Sisti et al. | 55/67 |
| 4,414,857 | 11/1983 | Brazhnikov et al. | 73/863.11 |
| 4,442,217 | 4/1984 | Deans | 73/23.1 X |

FOREIGN PATENT DOCUMENTS 1291724 10/1972 United Kingdom .................. 73/23.1

OTHER PUBLICATIONS

Grob, K., *Movements of the Sample Plug in the Column Inlet After On-Column Injection in Capillary Gas Chromatography.* In J. of Chromat., 283, (1984), pp. 21–35, 1984.

*Primary Examiner*—Stewart J. Levy
*Assistant Examiner*—Joseph W. Roskos
*Attorney, Agent, or Firm*—Ladas & Parry

[57]    ABSTRACT

A method of chromatographic analysis of mixture of liquid substances in which a sample of the substances is injected to an inlet portion of a chromatographic column wherethrough a flow of carrier gas is conveyed entraining vapors of the substances from the column to a detector. According to one feature of the invention, the flow of carrier gas is divided into two parts; one part of the flow being conveyed at the point of sample injection and during its separation through the column in a direction from the inlet to the outlet, whereas in the detector this part of the flow of carrier gas is conveyed through the column in a direction from the outlet to the inlet. The second part of the flow of carrier gas is continuously passed through the detector. A gas chromatograph comprises an injector having a passage for introducing the sample connected to a pipe for feeding a carrier gas, a chromatographic column, a detector, and a means for sealing this passage. The gas chromatograph further comprises an additional pipe for feeding the carrier gas connected to the outlet from the column, a flow restrictor of constant cross-section secured at the outlet from the detector, and a gas pressure regulator arranged in the additional pipe.

9 Claims, 3 Drawing Sheets

METHOD OF CHROMATOGRAPHIC ANALYSIS OF A MIXTURE OF LIQUID SUBSTANCES AND A GAS CHROMATOGRAPH FOR CARRYING OUT THE METHOD

FIELD OF THE INVENTION

The present invention relates to the art of physical and chemical methods employed for analyzing liquid substances, particularly to gas chromatography, and more particularly to a method of chromatographic analysis of mixtures of liquid substances and to a gas chromatograph for carrying out such a method.

The invention can find application in analyzing multicompound liquid mixtures of substances of a wide range of boiling temperatures in such industrial fields as chemical, petroleum, pharmaceutical, food industries and the like.

BACKGROUND OF THE INVENTION

There is known a method of chromatographic analysis of mixtures of liquid substances (cf., e.g., U.S. Pat. No. 3,798,973) in which a sample of substances to be analyzed is introduced by a syringe to the evaporator of a gas chromatograph by piercing a septum of a self-sealing material and the sample in injected to the interior of an evaporation chamber pneumatically communicating with the inlet of a chromatographic column. Vapours of the sample generated in the interior of the evaporation chamber are entrained by the flow of a carrier gas to the chromatographic column where the mixture of substances under analysis is chromatographically separated into separate constituents. The separated constituents of the sample are detected at the outlet from the chromatographic column by a suitable detector (heat conductivity detector, plasma-ionization detector, etc.) to register the signal of the detector by a recorder and use the chromatogram for calculating the concentration of the substances under analysis.

In most of the prior art gas chromatographs using the aforedescribed method of analysis precision and reproducibility of the results of the analysis are influenced by the septum of a self-sealing material (such as silicone rubber) provided in the evaporator of the gas chromatograph in the passage for receiving the syringe needle. Such a septum usually leads to ghost peaks appearing in the chromatogram during programmable heating of the column even when a sample is not injected into the evaporator. When introducing the sample by a syringe the needle of which pierces the self-sealing septum, particles of the septum material are cut off the septum and are carried by the needle to the interior of the evaporation chamber or to the inlet of the chromatographic column. These particles can be the source of gas emission distorting the results of chromatographic analysis. In addition, the self-sealing septum suffers from a rapid loss of hermeticity and needs frequent replacement.

There is also known a method of chromatographic analysis of mixtures of liquid substances using a device for introducing the sample to a chromatographic column without a septum (cf., e.g., U.S. Pat. No, 4,414,857). According to this method, a sample of liquid mixture is introduced by a syringe or some other sample carrier to the evaporator of a gas chromatograph through an open passage or channel sealing this channel by a sealing element connected to the sample carrier in the course of sample injection, evaporation and transfer of the vapours of the sample material from the evaporator to the chromatographic column. The vapours of the sample material are transferred from the evaporator to the chromatographic column by a flow of carrier gas, which forces the vapours through a flow restrictor of constant cross-section arranged between the evaporation chamber and the inlet to the chromatographic column. After transferring the vapours of the sample material from the evaporator to the chromatographic column admission of the carrier gas to the evaporator is terminated and the flow of this gas is directed to the inlet of the chromatographic column after the outlet from the flow restrictor of constant cross-section. A minor part of the flow of carrier gas entering the evaporation chamber through the flow restrictor acts to clean the interior of the evaporator from the remainder of the sample material venting this remainder to the atmosphere.

The heretofore described method of chromatographic analysis is very efficient and makes it possible to obviate many disadvantages of the prior art methods employing self-sealing septums. However, it ensures analysis only when a preliminarily volatilized sample is fed to the column. This in turn limits the range of liquid substances to be analyzed making it impossible to analyze certain substances decomposable under the action of high temperatures in the evaporator of the gas chromatograph.

There is known one more method of chromatographic analysis, in which a liquid sample is introduced by a syringe having a special needle directly to the inlet of a chromatographic column (on-column injection) at a temperature below the boiling point of the substances being analyzed. The syringe needle is inserted to the column through a passage for receiving a sample carrier closed by a rotary valve. Before injecting the sample the passage for receiving the sample is opened by turning the valve to a respective position. Subsequent to introducing the sample the passage for receiving the sample carrier is closed and the temperature in the column is gradually raised, while transferring the substances being analyzed in a vaporous state by the carrier gas to the main separating section of the column, where the sample material is separated into constituents to be detected at the outlet from the column by a suitable detector (cf., e.g., U.S. Pat. No. 4,269,608).

The gas chromatograph for carrying out this method comprises a capillary chromatographic column secured inside a constant-temperature chamber with a programmable temperature control, a passage for introducing the sample pneumatically communicating with the capillary chromatographic column, a means for sealing and unsealing the passage for receiving a sample carrier in the form of a rotary valve provided in this passage, a pipe for feeding a carrier gas communicating with the passage for introducing the sample, and a detector provided at the outlet of the chromatographic column.

A liquid sample is injected to the inlet of the column in the absence of hermetic sealing of the passage for introducing the sample, i.e., without a flow of carrier gas from the inlet to the outlet of the chromatographic column. This results in uncontrollable losses of the substance under analysis due to the escape of vapours of the solvent through the passage for receiving the sample carrier to the atmosphere and in a tendency of some of the liquid sample to stick to the outer surface of the syringe needle. This latter effect is generally caused by drawing of a quantity of the sample to an annular space between the outer surface of the syringe needle and the walls of the capillary column by virtue of capillary forces (cf., e.g., K.Grob, Jr., Journal of Chromatography, 283, 1984, pp. 21 to 25), which affects the accuracy of chromatographic analysis.

In addition, the known method and device for carrying out this method fail to carry out a chromatographic analysis when splitting the sample at the inlet to the main section of the chromatographic column, which limits the range of their practical application. The gas chromatograph for effecting the method is structurally overcomplicated due to the provision of a rotary valve in the passage for receiving the sample carrier, which adversely affects a combination of the gas chromatograph of this type with automatic metering devices for liquid samples (automatic samplers). Attempts to expand the functional capabilities of the gas chromatograph of this type resulted in a greater structural overcomplication, and as a consequence in reduced reliability (c.f., EP, B, No. 0,140,020).

SUMMARY OF THE INVENTION

It is the principal object of the present invention to provide such a method of chromatographic analysis, which would ensure analyzing a wide range of volatile liquid substances through selecting the optimum conditions for introducing liquid samples to the chromatographic column, viz., direct (on-column) injection of a sample to the column without preliminary evaporation, injection of a sample accompanied by division thereof in a flow of carrier gas (split mode), without division (splitless mode), and injection of a sample with preliminary concentration by blowing the vapours of the solvent contained in the sample.

Another object of the invention is to reduce the time required for analyzing multicomponent mixtures of liquid substances having a wide range of boiling points of their components by venting to the atmosphere the heavy components of the mixture not of interest for the purposes of the analysis by a backflow of carrier gas through the chromatographic column.

One more object is to increase the accuracy of chromatographic analysis through reducing the losses of substances being analyzed during introducing the sample to the inlet of the chromatographic column.

Another object is to increase the accuracy of chromatographic analysis through cleaning the chromatographic column from the remainder of the sample in the intervals between analyzing various mixtures of substances and preventing mutual contamination of the successively analyzed sample materials.

One more object is to ensure a higher reproducibility of the results of chromatographic analysis in terms of time through reducing contamination of the detector by vapours of a stationary liquid phase contained in the chromatographic column.

Another object is to ensure carrying out chromatographic analysis using both packed and capillary chromatographic columns without resorting to substantial alteration of the systems for injecting the sample and detecting the substances under analysis.

Yet another object is to provide a gas chromatograph of a simple and reliable construction dispensing with the use of movable sealing and switching elements (such valves, gates, etc.) contacting with the sample material throughout the travel path thereof from the sample injection system to the system for detecting the separated sample components.

A major object of the invention is to ensure stable functioning of the detector by stabilizing the flow rate of the carrier gas therethrough and by preventing the detector from being influenced by the operating conditions of the sample injection system and chromatographic column.

One more object is to provide a gas chromatograph which is simple and inexpensive in manufacture, and includes simple manufacturing operations for producing functional elements not necessitating highly qualified attending personnel.

These and other objects of the invention are attained by that in a method of chromatographic analysis of mixtures of liquid substances in which a sample of the substances to be analyzed is introduced by a sample carrier to an inlet of a chromatographic column at a temperature below the boiling point of the substances under analysis, a flow of carrier gas being conveyed through the column gradually increasing the temperature in the column and transferring the substances under analysis to a vaporous state, these substances entrained by the carrier gas and separated after passing through the chromatographic column being detected by a detector, according to the invention, the flow of carrier gas is divided at least into two parts of which one part is fed to the chromatographic column, whereas the other part is fed to the detector, at the point of injecting the sample and in the course of chromatographic separation of the substances under analysis part of the flow of carrier gas fed to the column is conveyed through this column in a direction from the inlet to the outlet, the other part of the flow fed to the detector is mixed with the part of the flow of carrier gas exiting the column and the thus united flow of carrier gas is conveyed through the detector, and subsequent to the passage of the substances under analysis from the column to the detector one part of the flow of carrier gas fed to the column is conveyed through the column in a direction from the outlet to the inlet venting it to the atmosphere and thereby cleaning the column from the remainder of the sample material, whereas the other part of the flow of carrier gas is continued to be fed directly to the detector stabilizing the pressure of the carrier gas at its inlet and thereby maintaining continuous working conditions of the detector.

Thanks to separation of the flow of carrier gas into two parts of which one part can be conveyed through the chromatographic column in any direction, that is from the inlet to the outlet or from the outlet to the inlet, whereas the other part of the flow of carrier gas is continuously fed to the detector, and also thanks to that in any direction of the flow of carrier gas through the column the working conditions of the detector remain invariable by virtue of stabilized flow of carrier gas therethrough, it is possible to effect various modes of injecting the sample to the inlet of the column without affecting the functioning of the detector.

Another advantage of the proposed method of chromatographic analysis is that thanks to varying the direction of the flow of carrier gas in the chromatographic column after conveying all the substances under analysis from the column to the detector it is possible to reduce the time for analyzing multicomponent mixtures by blowing the high-boiling components of the mixture not of interest for the purposes of the analysis by the flow of carrier gas passed through the chromatographic column in a direction from the inlet to the outlet and conveyed to the atmosphere.

One more advantage of the proposed method resides in that it offers reduced losses of the substances under analysis as the sample is introduced to the inlet of the chromatographic column thanks to that at the point of introducing the sample part of the flow of carrier gas fed to the column is conveyed therethrough in a direction from the inlet to the outlet. This prevents the vapours of substances from being discharged from the inlet of the column to the atmosphere and some quantity of the sample material from being pulled to the annular space between the outer surface of the sample carrier, such as the syringe needle, and the inner walls of the column, which in turn results in a higher accuracy of the chromatographic analysis.

In addition, changing the direction of the flow of carrier gas in the chromatographic column after the passage of the substances under analysis from the column to the detector cleans the chromatographic column from the remainder of the sample material, which prevents mutual contamination of the successively analyzed sample materials and contributes to a still higher accuracy of chromatographic analysis.

Yet another advantage of the proposed method is that due to changing the direction of the flow of carrier gas in the chromatographic column after transferring all the substances under analysis from the column to the detector the latter is not communicated with the chromatographic column in the intervals between analysis of various sample materials, whereby the detector is not contaminated with vapours of substances remaining in the column, particularly with vapours of the stationary liquid phase used in the column for separating the substances being analyzed. This ensures a higher stability of the output signal of the detector in time and, as a consequence, improves the reproducibility of the results of chromatographic analysis.

When analyzing mixtures of substances dissolved in a substantial quantity of the solvent having a boiling point below the boiling point of the substances being analyzed, it is advisable that after injecting the sample to the inlet of the chromatographic column and before increasing the temperature in the column one part of the flow of carrier gas fed to the column is conveyed through the column in direction from the outlet to the inlet thereby venting the substances to the atmosphere and liberating the substances under analysis from the solvent.

This affords to effect one more mode of injecting a sample to the column accompanied by preliminary concentration thereof through blowing the solvent vapours. This also afford to expand the range of liquid substances to be analyzed and further ensures a more sensitive chromatographic analysis due to increased volume of sample injected to the inlet of the chromatographic column.

Preferably, as the temperature in the chromatographic column increases, the temperature of the inlet of the column containing the sample is maintained at a level higher than the temperature of the rest of the column.

Such a procedure provides additional compression of the band of substances as they are entrained by the carrier gas from the inlet of the column to the main separating part thereof and, as a consequence, promotes a higher efficiency of the process of chromatographic separation.

When using a highly efficient capillary with an inside diameter of 0.25 mm or less as the chromatographic column, it is possible in the course of increasing the temperature in the column to divide part of the flow of carrier gas fed to the chromatographic column and conveyed therethrough in a direction from its inlet to the outlet after passing the inlet of the column with the vapours of the substances being analyzed into two parts of which one part is conveyed through the rest of the chromatographic column, and the other part with some of the vapours of the sample material is vented to the atmosphere.

This affords one more mode of injecting a sample to the capillary chromatographic column accompanied by division of the sample with the flow of carrier gas (split injection), which likewise expands the range of liquid substances being analyzed and optimizes conditions of chromatographic separation in the capillary chromatographic column.

The aims of the invention are also attained by that in a gas chromatograph for carrying out the proposed method of chromatographic analysis of mixtures of liquid substances comprising a chromatographic column with a constant-temperature chamber, an inlet of this column accommodating a sample injector having a passage for introducing the sample of substances under analysis by a sample carrier pneumatically communicating with a pipe for feeding a carrier gas, an outlet thereof accommodating a detector for detecting the substances under analysis separated in the chromatographic column, and a means for sealing and unsealing the passage for introducing the sample, according to the invention, the chromatograph is provided with an additional pipe for feeding the carrier gas connected to the outlet of the chromatographic column, a flow restrictor of constant cross-section secured at the inlet to the detector after the point of connection of the additional pipe for feeding the carrier gas with the outlet from the column, a gas pressure regulator secured in the additional pipe for feeding the carrier gas and intended for stabilizing the flow rate of the carrier gas, and a means for controlling the flow of carrier gas secured in the pipe for feeding the carrier gas connected to the passage for introducing the sample, the means for sealing and unsealing the passage for introducing the sample having the form of a sealing element connected to the sample carrier and operatively secured at the inlet of the passage for introducing the sample jointly with the sample carrier.

One advantage of this gas chromatograph is structural simplicity and reliability in operation due to the absence of sealing or switching elements (such as valves, gates, etc.) contacting with the material of the sample on its travel path from the sample injection system to the system for detecting the separated components. The only sealing element employed is one that is connected to the sample carrier to seal the inlet of the passage for receiving the sample with the sample carrier at the point of introducing the sample to the inlet of the chromatographic column and during separation of the sample constituents in the chromatographic column. As the inlet of the passage for receiving the sample is sealed, the flow of carrier gas travels in the chromatographic column in a direction from the inlet to the outlet, whereas when the inlet of the passage for receiving the sample is unsealed by withdrawing the sample carrier from the passage, the flow of carrier gas travels inside the chromatographic column in a direction from the outlet to the inlet thereby cleaning the column from the remainder of the sample material.

This arrangement of the gas chromatograph affords analysis of a wide range of volatile liquid substances under different sample injection modes, and separation of the sample material by changing the travel path of the carrier gas in the chromatographic column at any time of the chromatographic analysis in combination with varying the temperature inside the column.

Also, this construction of the gas chromatograph allows reduction in the time of analysis thanks to reversing the flow of carrier gas in the column subsequent to the escape of all the substances being analyzed from the column to the detector and blowing to the atmosphere part of the high-boiling materials of the sample not of interest for the purposes of the analysis. The proposed gas chromatograph further ensures that the chromatographic column is cleaned in the intervals between analyses of different substances from the remainder of the sample material, prevents mutual contamination of successively analyzed sample materials, and reduces contamination of the detector by vapours of the substances conveyed from the column, such as vapours of the stationary liquid phase, used as a sorbent in the column.

In a modification of the proposed gas chromatograph most suitable for operation with a packed chromatographic column it is preferable that the means for controlling the flow of carrier gas to be fashioned as a pressure regulator, an outlet of which is provided with a controllable shut-off valve by-passed by a flow restrictor of constant cross-section.

Such an arrangement allows to stabilize conditions for sample introduction and chromatographic separation through stabilizing the pressure of carrier gas at the inlet to the column and to reduce the flow rate of carrier gas by closing the pipe for feeding the carrier gas communicating with the passage for introducing the sample subsequent to terminating the analysis and unsealing this passage.

In one preferred embodiment of the proposed gas chromatograph it is provided with a means for heating and cooling the inlet to the chromatographic column to which a sample is introduced.

This ensures independently optimized temperature conditions for injecting the sample and its separation, respectively, to the inlet of the chromatographic column and the separating section thereof. More particularly, in the course of increasing the temperature in the column the temperature of its inlet portion containing the sample is maintained at a higher level than the rest of the column. Therefore, compression of the band of substances under analysis is facilitated as these substances are conveyed by the carrier gas from the heated inlet portion of the column to a cooler separating section thereof to result in a more efficient chromatographic separation of the sample material.

In another embodiment of the proposed gas chromatograph more suitable for operation with a capillary column there is a provision for a gas flow divider in the form of a T-joint secured between the inlet of the column and the rest of the column, the inlet of the T-joint being connected to the inlet of the chromatographic column, whereas one outlet of the T-joint is connected to the rest of the chromatographic column, the other outlet being connected through a controllable shut-off valve and a controllable flow restrictor with the atmosphere.

Such an arrangement allows one more sample injection procedure accompanied by division of the sample and flow of carrier gas (split mode), which again expands the range of materials to be analyzed and optimizes conditions for chromatographic separation in the capillary chromatographic column.

Advisably, when using a capillary chromatographic column, the means for controlling the flow of carrier gas secured in the pipe for feeding the carrier gas connected to the passage for introducing the sample is fashioned as a gas flow regulator.

Such an arrangement still more simplifies the construction of the chromatograph, because the arrangement in the pipe for feeding the carrier gas of a controllable shut-off valve normally employed when operating with a packed column can be dispensed with.

The invention will now be described in greater detail with reference to various specific embodiments thereof taken in conjunction with the accompanying drawings, in which.

BEST MODE OF CARRYING OUT THE INVENTION

The essence of the herein proposed method of chromatographic analysis will become more fully apparent from the description of various preferred embodiments of a gas chromatograph for carrying out the method that follows.

Figure 1:
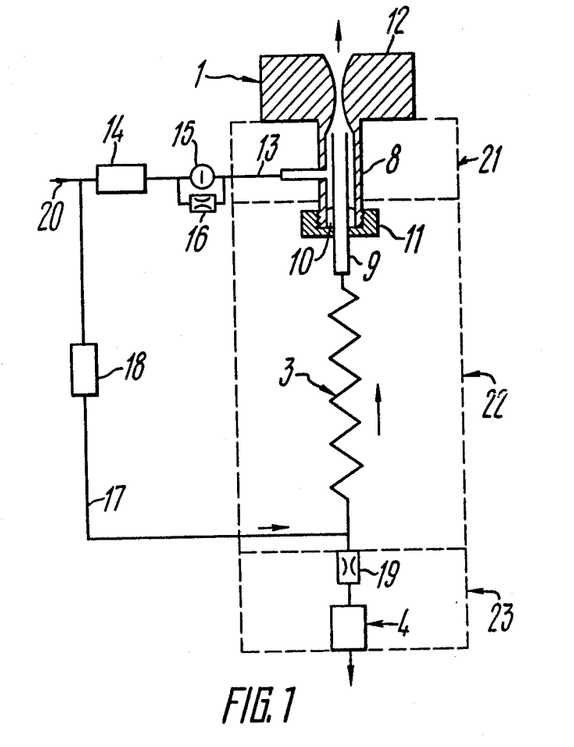
FIG. 1 is a partially sectional view of the proposed gas chromatograph before carrying out a chromatographic analysis.
Figure 2:
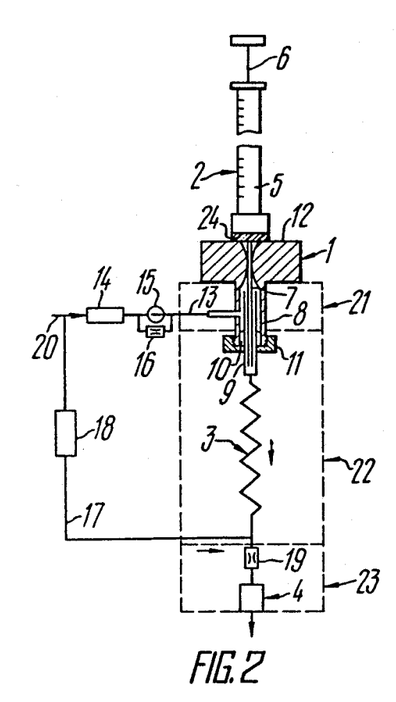
FIG. 2 shows the gas chromatograph represented in FIG. 1 at the point of introducing a sample by a sample carrier and during carrying out a chromatographic analysis of the sample material.

Referring now to FIGS. 1 and 2, there is shown the simplest modification of the proposed chromatograph in two working positions, viz., in the position immediately preceding the introduction of a sample (FIG. 1), and in the position during the introduction of the sample and carrying out the chromatographic analysis (FIG. 2).

A sample injector of the gas chromatograph is indicated by 1, a sample carrier by 2, a chromatographic column is indicated by 3, and a detector of positions by 4. The chromatographic column 3 is of any known suitable design, and is generally a tubular member of inert material, such as glass, filled with particles of a sorbent, or a capillary made of an inert material (such as glass, fused silica, or the like) the inner surface of which is covered by a film of the fixed liquid phase. The sample carrier 2 can likewise have any known suitable construction, and in this embodiment has the form of a syringe with a casing 5 of a transparent material, such as glass, having a movable mandrin 6 provided in a longitudinal axial passage thereof. A hollow needle 7 is connected to the casing 5 of the syringe, the inner passage of this needle being continuation of the passage of the casing 5. The injector 1, being an integral part of the proposed gas chromatograph, has a cylindrical housing fabricated from an inert heat-resistant material, such as stainless steel, an axial longitudinal passage of which receives an inlet 9 of the chromatographic column 3 secured by means of a sealing ring element 10 fabricated from a heat-resistance soft material, such as graphite.

The sealing element 10 is pressed by a coupling nut 11 to provide a hermetic seal between outer walls of the inlet 9 of the column 3 and inner walls of a housing 8 of the injector 1. Part of the housing 8 of the injector 1 opposite to the point of attachment of the column has an expanded cylindrical head 12 with a longitudinal axial passage thereof serving as the passage for introducing the sample by the sample carrier 2. In the embodiment discussed herein connection of the sample carrier 2 with the inner passage of the inlet 9 of the chromatographic column 3 is ensured by introducing the hollow needle 7 of the syringe to the interior of the inlet portion 9 of the chromatographic column 3. The interior of the inlet portion 9 of the chromatographic column is free of the particles of sorbent to the point of the maximum penetration of the tip of the syringe needle 7. Connected to the injector 1 is a pipe 13 for feeding a carrier gas, such as nitrogen, which communicates through an inner annular clearance between the inlet 9 of the chromatographic column 3 and inner walls of the housing 8 of the injector 1 with the passage for receiving the sample.

The pipe 13 for feeding the carrier gas includes a means 14 for controlling the flow of the carrier gas, which can have any known suitable construction. In this particular embodiment schematically illustrated in Figs 1 and 2 the means 14 for controlling the flow of carrier gas is fashioned as a pressure regulator normally employed in the known gas chromatographs for maintaining a continuous pressure at the inlet to the chromatographic column 3. In the modification of the proposed gas chromatograph a known pneumatic-type pressure regulator is provided with a shut-off valve 15 arranged at the outlet from the pressure regulator and by-passed through a flow restrictor 16 of constant cross-section. In other alternative modifications the means 14 for controlling the flow of carrier gas can have the form of any known suitable air-operated or mechanical flow regulator, such as a flow restrictor with adjustable cross-section, or a needle valve, or the like.

The gas chromatograph according to the invention has one more pipe 17 for feeding the carrier gas connected to the outlet from the chromatographic column 3, and having a pressure regulator 18. Provided at the inlet to the detector 4, such as a plasma-ionization detector, is a flow restrictor 19 of constant cross-section arranged after the point of connection of the additional pipe 17 for feeding the carrier gas to the outlet of the chromatographic column 3. The pipe 13 for feeding the carrier gas connected to the passage for introducing the sample and the pipe 17 for feeding the carrier gas connected to the outlet from the chromatographic column 3 are integrated into a common pipe 20 for feeding the carrier gas connected to a source (not shown) of the carrier gas. The sample injector 1, chromatographic column 3 and detector 4 are placed in constant-temperature chambers 21, 22 and 23, respectively, schematically represented in FIGS. 1 and 2 by dotted lines. The sample carrier 2 is provided with a sealing element 24, which in the embodiment herein described is fashioned as a sleeve fabricated from an elastic inert material, for example silicone rubber, and secured on syringe needle 7 at the base of the casing 5. The sealing element 24 with the sample carrier 2 function as a means for sealing and unsealing the inlet in the head 12 of the sample injector 1. Sealing of the passage for introducing the sample is done by operatively placing the sealing element 24 connected with the sample carrier 2 at the inlet of the passage for introducing the sample as the needle 7 is inserted into the inlet portion 9 of the chromatographic column 3, as seen best in FIG. 2. The flow restrictors 16 and 19 are fashioned in the herein described embodiment as capillary tubes with flattened sections.

The heretofore described embodiment of the proposed gas chromatograph operates in the following manner.

Initially and prior to carrying out a chromatographic analysis the valve 15 is closed, and a flow of carrier gas is continuously conveyed along the pipe 17 to the outlet from the chromatographic column 3. At the outlet from the chromatographic column the gas flow is split into two flows. Part of the flow of carrier gas enters the chromatographic column 3 to move therein in the direction from the outlet to the inlet and be discharged through the passage for introducing the sample in the head 12 of the injector 1 to the atmosphere, thereby blowing-back the column and preventing the access of the atmospheric air to the interiors of the injector 1 and column 3. Another part of the flow of carrier gas is forced from the pipe 17 through the flow restrictor 19 of constant cross-section to the detector 4 to be also discharged to the atmosphere therethrough. Thanks to the provision of the pressure regulator 18 in the pipe 17 for feeding the carrier gas and of the flow restrictor 19 at the inlet to the detector, the rate of flow of the carrier gas is maintained continuous to stabilize its operation. The ratio between part of the flow of the carrier gas conveyed as a backflow through the chromatographic column 3 and part of the flow of the carrier gas conveyed through the detector 4 is determined by the relationship between the pneumatic resistances of the chromatographic column 3 and flow restrictor 19, respectively. When using as the chromatographic column 3 a column fashioned as a tube of an inert material having an inside diameter of 2–3 mm and filled with particles of sorbent, and as the detector 4 a plasma-ionization detector, the gas resistance of the flow restrictor 19 is preferably selected so that the rate of gas flow through the detector be within 50–60 ml/m. The flow rate of carrier gas through the chromatographic column 3 conveyed in the direction from the outlet to the inlet should preferably be 15–20 ml/m. This flow rate is controlled by a flow meter (not shown) at the point of discharge of the part of the carrier gas flow from the column 3 through the passage for introducing the sample in the head 12 of the injector to the atmosphere. The temperature of the bottom part of the injector 1 connected to the inlet 9 of the chromatographic column is maintained by the constant-temperature chamber 21 at 10°–15° C. higher than the room temperature but below the boil point of the constituents of the liquid mixture of substances under analysis. The same temperature values are maintained by the constant-temperature chamber 22 in the chromatographic column 3. The temperature of the detector 4 and of the constant cross-section flow restrictor 19 is maintained by the constant temperature chamber 23 through the cycle of analysis and during intervals between analyses to be higher than the condensation point of vapours of the substances being analyzed. In this position of the gas chromatograph only a fraction (1–2 ml/m) of the carrier gas is let out to the atmosphere from the inlet of the pressure regulator 14 through the constant cross-section flow restrictor 16.

Before starting the analysis, a measured quantity of the liquid mixture of substances to be analyzed is taken by the syringe 2, and the needle 7 of the syringe 2 is introduced through the passage in the head 12 of the injector 1 to the inlet portion 9 of the chromatographic column 3 to the stop when the sealing element 24 secured on the needle 7 at the base of the casing 5 of the syringe 2 hermetically seals the inlet to the passage for letting - in the sample (FIG. 2). At this point in time the valve 15 is opened, and analysis of the liquid mixture of substances is carried out in accordance with the proposed method of chromatographic analysis. The flow of the carrier has conveyed along the pipe 20 is split into two flows. One part of the flow of carrier gas is conveyed through the pressure regulator 14 and open valve 15 to the inlet of the chromatographic column 3 to be conveyed therethrough in the direction from the inlet to the outlet (as shown by the arrow in FIG. 2). With this direction of the flow of carrier gas through the column 3 the mandrin 6 of the syringe 2 is pressed to introduce a sample of substances to be analyzed to the interior of the inlet 9 of the chromatographic column 3 onto a bed of sorbent (not shown) arranged at the inlet portion 9 of the column 3 somewhat below the tip of the needle 7 of the syringe 2. At the point of introducing the sample the temperature of the column 3 including the inlet portion 9 thereof accommodating the sample is maintained at below the boil point of the substances being analyzed. Subsequent to introducing the sample the temperature in the column is increased to cause vaporization of the substances being analyzed. Vapours of these substances are carried by the flow of carrier gas through the column 3 in the direction from the inlet to the outlet, which is accompanied by chromatographic separation thereof into separate constituents. The second part of the flow of carrier gas is fed along the pipe 17 through the pressure regulator 18 to the inlet of the detector 4, where it is mixed with part of the flow of the carrier gas conveyed through the column 3, whereafter the thus united flow of carrier gas containing the separated substances escaping from the column 3 is passed through the flow restrictor 19 of constant cross-section and through the detector 4, where the separated substances are detected.

After the escape from the chromatographic column of all constituents of the mixture of substances of interest for the purpose of chromatographic analysis the needle 7 of the syringe is retracted from the inlet 9 of the chromatographic column 3 thereby unsealing the passage for introducing the sample in the head 12 of the injector 1, and the shut-off valve 15 is closed for the chromatograph gas lines to assume the position illustrated in FIG. 1. In this position the flow of carrier gas is delivered along the pipe 17 to the outlet from the chromatographic column 3, where it is split into two flows. Part of the flow of carrier gas is conveyed through the chromatographic column 3 in the direction from the outlet to the inlet and is discharged to the atmosphere through the passage for introducing the sample in the head 12 of the injector. This is accompanied by cleaning of the column 3, especially of its inlet portion 9, from high-boiling remainder of the mixture of substances being analyzed. The other part of the flow of carrier gas is admitted through the flow restrictor 19 to the detector 4 to be discharged to the atmosphere therefrom. No variations in the flow rate of the carrier gas through the detector 4 occur thanks to the provision of the pressure regulator 18 and constant cross-section flow restrictor 19. After finishing the chromatographic analysis the temperature of the constant-temperature chamber 22 of the chromatographic column is returned to the initial temperature exceeding by 10°-15° C. the room temperature.

It is to be noted that the proposed gas chromatograph can be used most advantageously in combination with known automatically operated devices for introducing liquid samples by using a syringe as the sample carrier. Holding the syringe in the position shown in FIG. 2, when the sealing element 24 acts to seal the passage for introducing the sample in the head 12 of the injector 1, is executed by a mechanism for moving the syringe, which is an indispensable part of all known devices for automatically injecting liquid samples (automatic samplers). Operation of the automatic liquid samplers makes a good combination with automatic switching of the valve 15 and with automatic temperature programming of the constant-temperature chamber 22 of the chromatographic column. It is also important, that the aforedescribed modification of the gas chromatograph can be successfully used in combination with a capillary chromatographic column without changing the general layout of the chromatograph and mode of its operation.

The heretofore described modified form of the proposed gas chromatograph makes it possible to carry out such a method of chromatographic analysis in which a sample of liquid substances is preliminarily concentrated through blowing the vapours of a highly volatile solvent containing dissolved low-volatile (high-boiling) materials being analyzed. With this aim in view, after injecting the liquid sample to the bed of sorbent at the inlet 9 of the chromatographic column 3 (position illustrated in FIG. 3) the needle 7 of the syringe 2 is withdrawn from the inlet 9 of the chromatographic column 3 and from the passage for introducing the sample, the valve 15 is closed, and the gas chromatograph is brought to the working position represented in FIG. 1. In this position part of the carrier gas is conveyed through the chromatographic column in the direction from the outlet to the inlet blowing the vapours of the highly volatile solvent from the inlet 9 of the column 3 through the passage for introducing the sample in the head 12 of the injector 1 to the atmosphere. The procedure of blowing the vapours of the solvent is terminated after 10-15 s. After this the passage for introducing the sample is sealed by inserting the syringe 2 in a position shown in FIG. 2, the valve 15 is opened, and the temperature of the constant-temperature chamber 21 of the chromatographic column 3 is raised to carry out the process of chromatographic analysis of the concentrated components of the liquid sample in the aforedescribed sequence. The heretofore described technique of concentrating the high-boiling components of the liquid sample by preliminarily blowing the vapours of the highly volatile solvent can be used for increasing the sensitivity of chromatographic analysis. A relatively large quantity of the liquid mixture of substances (10 to 15 microliters and more) can be injected to the inlet 9 of the chromatographic column.

Figure 3:
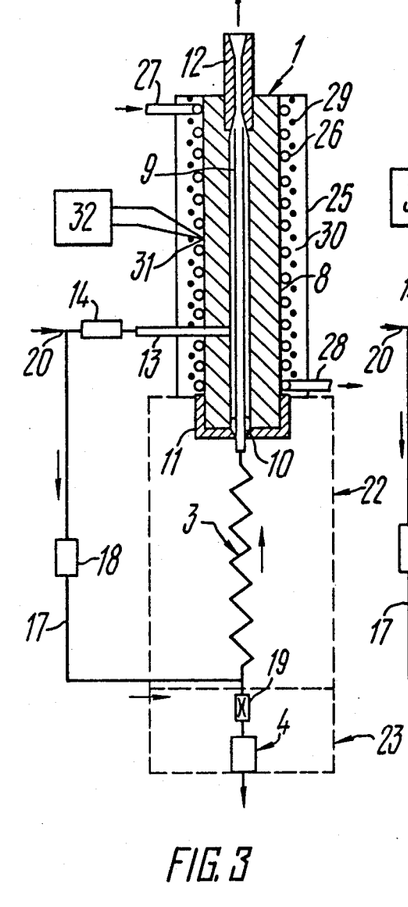
FIG. 3 is another modified form of the proposed gas chromatograph with a capillary chromatographic column and a means for heating and cooling the inlet to the column at the point in time preceding the chromatographic analysis.
Figure 4:
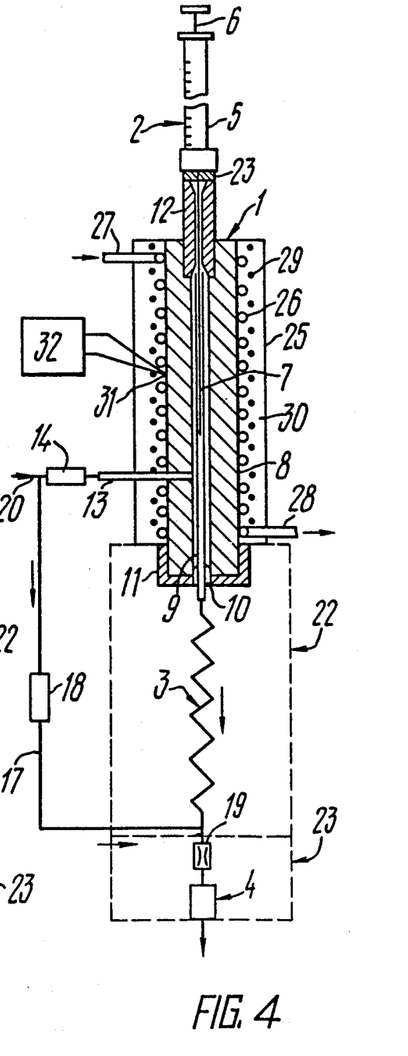
FIG. 4 shows the gas chromatograph of FIG. 3 at the point of injecting the sample and during chromatographic separation thereof.

Referring now to FIGS. 3 and 4, there are shown two working positions of another alternative embodiment of the proposed gas chromatograph intended mainly to operate with capillary chromatographic columns, like elements of the chromatograph in these FIGS. 3 and 4 bearing the same reference numerals as in FIGS. 1 and 2. As distinct from the heretofore described modification of the proposed chromatograph, the chromatograph shown in FIGS. 3 and 4 partially schematically and partially in section is characterized by that it is provided with a means 25 for heating and cooling the inlet 9 of the chromatographic column 3. This means 25 in this particular modification comprises a cooling coil 26 with inlet and outlet pipes 27 and 28 for feeding and discharging, accordingly, of a cooling agent, such as water, and a heating coil 29 separated from the cooling coil 26 by a layer 30 of heat-insulating material. The cooling coil 26 is arranged immediately on the walls of the housing 8 of the injector 1. A temperature meter 31, such as a thermocouple, is provided at the outer wall of the housing 8 of the injector 1, this thermocouple being connected to an automatic temperature programmer of any known suitable construction normally used in gas chromatography for programming the constant-temperature chamber of the chromatographic column.

Another distinctive feature of this modification of the gas chromatograph, in contrast to the chromatograph shown in FIGS. 1 and 2, is that the means 14 for controlling the flow of the carrier gas in the pipe 13 for feeding the carrier gas is fashioned as an air-operated of mechanical flow governor. The embodiment of the proposed gas chromatograph with a capillary column 3 represented in FIGS. 3 and 4 operates in the following manner.

At the point in time preceding the analysis the flow of carrier gas fed along the pipe 20 is split into two flows. The smaller part of the flow (1 to 2 ml/m) of the carrier gas is conveyed along the pipe 13 through the gas flow governor 14 to the inlet of the chromatographic column 3 to be vented to the atmosphere through the passage for introducing the sample in the head 12 of the injector 1. Another part of the flow of carrier gas is conveyed along the pipe 17 through the pressure regulator 18 to the outlet of the chromatographic column 3, where it is also divided into two parts with the smaller part (5 to 6 ml/m) of the flow of carrier gas passing through the chromatographic column 3 in the direction from the outlet to the inlet and is vented to the atmosphere through the passage for introducing the sample in the head 12 of the injector 1. The greater part (50 to 60 ml/m) of the flow of carrier gas conveyed along the pipe 17 through the flow restrictor 19 of constant cross-section enters the detector 4 to be vented therefrom to the atmosphere. Therewith, the flow of carrier gas conveyed through the detector 4 is stabilized by the pressure regulator 18 and flow restrictor 19 of constant cross-section. The temperature of the housing 8 of the injector 1 and that of the inlet 9 of the chromatographic column 3 is maintained at this point by the means 25 for heating and cooling the inlet 9 of the column 3 at a level equal or close to room temperature, that is at a temperature substantially below the boiling point of the components of the liquid mixture of substances being analyzed. The temperature in the constant-temperature chamber 22 of the chromatographic column 3 is maintained at a level exceeding the room temperature by 5°–10° C., whereas the temperature of the constant-temperature chamber 23 of the detector 4 is maintained at a level exceeding the condensation point of vapours of the substances being analyzed. In these conditions operation of the gas chromatograph prior to initiating the analysis is stabilized.

Before initiating the analysis a measured quantity of a liquid mixture of substances to be analyzed is taken by the syringe 2, and the needle 7 of the syringe 2 is inserted through the passage for introducing the sample in the head 12 of the injector 1 to the inlet 9 of the chromatographic column to the stop, when the sealing element 24 acts to sealingly block the entry to the passage for introducing the sample.

At this point in time automatic redistribution of gas flows in the gas system of the chromatograph takes place. The flow of carrier gas conveyed along the pipe 13 through the gas flow governor 14 the annular clearance between the outer surface of the inlet 9 of the chromatographic column 3 and inner walls of the housing 8 of the injector 1 is delivered to the inlet of the chromatographic column 3 to pass through the column 3 in the direction from the inlet to the outlet. The flow of carrier gas conveyed along the pipe 17 through the pressure regulator 18 is fed to the outlet from the chromatographic column 3, where it is mixed with the flow from the column 3 and passes through the flow restrictor 19 of constant cross-section and detector 4 to be vented to the atmosphere. After injecting the sample to the inlet 9 of the chromatographic column 3 the temperature of this inlet portion 9 is programmably increased by the heating and cooling means 25 and programmer 32.

The syringe 2 remains in the position shown in FIG. 4 in which the sealing element 24 hermetically blocks the inlet of the passage for introducing the sample in the head 12 of the injector 1 and the flow of carrier gas entering the injector through the pipe 13 is conveyed through the chromatographic column 3 in the direction from the inlet to the outlet. The temperature of the rest of the chromatographic column 3 present in the constant temperature chamber remains invariable, that is this temperature is maintained at 5°–10° C. above the room temperature. An increase in the temperature of the inlet 9 to the chromatographic column 3 is accompanied by gradual transition of the components of the liquid mixture of substances to a vaporous state. Vapours of the substances are entrained by the carrier gas from the inlet 9 of the chromatographic column 3 to the rest of the column 3 of a lower temperature, where the vapours are condensed and a band of the substances is compressed on the bed of sorbent. As the substances being analyzed are carried from the inlet 9 of the column to the rest of this column 3, the temperature of the constanttemperature chamber 22 of the chromatographic column 3 is raised to carry out the process of chromatographic separation of the constituents of the mixture of substances under analysis according to the programmed temperature change in the column 3. These temperature conditions for introducing a sample of liquid substances and their chromatographic analysis in the capillary chromatographic column 3 prevent escape of the vapours of the substances under analysis from the inlet 9 of the column 3 to the annular clearance between the inlet 9 of the column 3 and inner walls of the housing 8 of the sample injector 1 and to the pipe 13. This facilitates compression of the band of substances during introduction of the sample and promotes a higher efficiency of chromatographic separation.

After finishing the chromatographic analysis, when all the constituents of the sample have passed through the chromatographic column and have been registered by the detector 4, the needle 7 of the syringe 3 is retrieved from the inlet 9 of the column 3 thereby unsealing the passage for introducing the sample in the head 12 of the sample injector 1. The gas system of the chromatograph is automatically switched over to the position illustrated in FIG. 3, when part of the carrier gas flow fed to the inlet of the chromatographic column moves in the column 3 from the inlet to the outlet to carry out cleaning of the column 3, especially of its inlet portion 9, from the remainder of the sample material. The inlet 9 of the column is then cooled by admitting the cooling agent to the cooling coil 26 and deenergizing the heating coil 29, and the temperature of the inlet 9 of the column is set to be equal or close to the room temperature. The temperature of the constant-temperature chamber 22 of the chromatographic column 3 is returned to the initial temperature level of the chamber 22 to thereby prepare the gas chromatograph to analyzing a successive sample of liquid substances.

Figure 5:
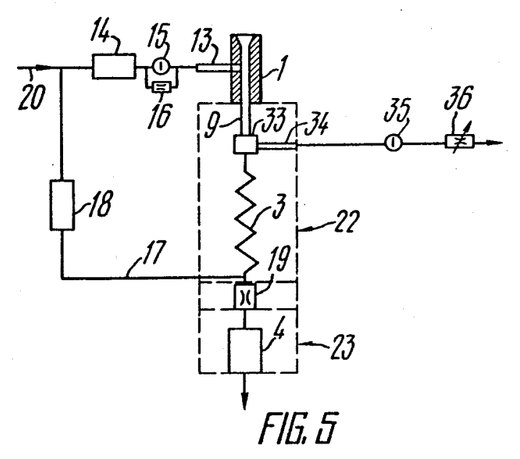
FIG. 5 is another modification of the proposed gas chromatograph with a capillary chromatographic column and a gas flow splitter.

With reference to FIG. 5, there is shown a schematic partially sectional view of a modified form of the proposed gas chromatograph with a capillary chromatographic column and a carrier gas flow divider.

Elements of the gas chromatograph shown in FIG. 5 are substantially similar to the elements of the gas choromatograph illustrated in FIGS. 1 and 2, and are indicated by like reference numerals. The modification of the gas chromatograph shown in FIG. 5 differs from the modified form of the gas chromatograph with reference to FIGS. 1 and 2 in that it is provided with a divider 33 of the flow of carrier gas in the form of a T-joint an inlet of which is connected to the inlet portion 9 of the chromatographic column 3, one outlet of the T-joint 33 being connected to the rest of the chromatographic column 3, whereas the other outlet of the T-joint is connected to a pipe 34 for venting the carrier gas to the atmosphere. This pipe 34 has a controllable shut-off valve 34 and a controllable flow restrictor 36 arranged in series. The inlet 9 of the chromatographic column 3 is fashioned here as a glass tube having an inside diameter of 1-3 mm partially filled with particles of a sorbent. One end of the outlet 9 of the column 3 is secured in the sample injector 1, whereas as the other end is secured in the inlet passage of the T-joint 33. The rest of the chromatographic column has the form of a capillary with an inside diameter of 0.5 mm or less, the inside walls of which are coated with a film (fixed liquid phase, such as methylsilicone elastomer). One end of the capillary tube is secured in the outlet passage of the T-joint 33, whereas the other end is connected to the flow restrictor 19 of constant cross-section.

The modified form of the proposed gas chromatograph operates in the following manner.

At a point in time preceding the introduction of the sample the valves 15 and 35 are closed. The flow of carrier gas is conveyed from the pipe 20 along the pipe 17 through the pressure regulator 18 to the outlet from the chromatographic column 3 where it is split into two portions or flows. One part of the flow of carrier gas (5–10 ml/m) passes through the chromatographic column 3 from its outlet to the inlet and is vented to the atmosphere through the inlet 9 of the column 3 and passage for introducing the sample in the injector 1 thereby cleaning the column 3, especially its inlet 9, and preventing the penetration of atmosphere air to the inlet of the column 3. The temperature of the inlet 9 and the rest of the chromatographic column 3 is maintained by the constant-temperature chamber 22 at 5°–10° C. above the room temperature. At the point of introduction of the sample of liquid mixture of materials by the syringe 2 the passage for introducing the sample in the injector 1 is sealed by closing the inlet to this passage with the help of the sealing element 24. After sealing the passage for introducing the sample the valves 15 and 35 are opened, and the sample is injected onto the bed of sorbent particles at the inlet 9 to the chromatographic column 3. Thereafter, while leaving the syringe 2 in a position in which the sealing element 24 threaded onto the needle 7 of the syringe 2 hermetically seals the passage for introducing the sample in the injector 1, the temperature of the chromatographic column 3 including its inlet 9 is raised by the constant-temperature chamber 22. As the temperature of the inlet 9 of the chromatographic column 3 is raised, the components of the liquid sample are volatilized for the vapours of the substances to be entrained by the flow of carrier gas and conveyed to the flow divider 33, where they are divided together with the flow of carrier gas into two parts. A minor part of the vapours of substances and a smaller part of the carrier gas (1–3 ml/m) are conveyed to the rest of the chromatographic column 3, where they are chromatographically separated into constituents. A major part of the vapours of substances with a larger part of the carrier gas (5–30 ml/m) are vented through the open controllable shut-off valve 35 and controllable flow restrictor 36 to the atmosphere. The ratio between the parts of the carrier gas discharged along the pipe 34 to the atmosphere and conveyed to the other (capillary) portion of the chromatographic column is determined by the relationship between the resistance to the gas flow produced by the controllable flow restrictor 36 and the resistance to the gas flow produced by the capillary portion of the column 3 and flow restrictor 19 of constant cross-section. Such conditions for introducing a sample to a capillary chromatographic column is known as a splitter-type injection. In the embodiment of the proposed gas chromatograph shown in FIG. 5 the sample can be injected in a splitless mode. With the splitless type of sample injection prior to injecting the sample onto the layer of sorbent present at the inlet 9 of the chromatographic column and after sealing the passage for admission of the sample carrier 2 only the valve 15 is opened, whereas the valve 35 remains closed. Therewith, vapours formed during an increase in the temperature of the column 3 are fully transferred by the carrier gas from the inlet 9 of the column 3 to the capillary portion thereof, where they are chromatographically separated.

INDUSTRIAL APPLICABILITY

The use of the proposed invention makes it possible to carry out any of the known modes for introducing samples of liquid substances to a chromatographic column, particularly, direct or "on column" type of injection without preliminary volatilization of substances, direct sample injection with preliminarily concentrating the sample by blowing the vapours of the solvent present in the sample, injecting a sample by dividing it in the flow of a carrier gas (split mode), injecting a sample without division (splitless mode), etc. This in turn ensures analysis of a wide range of volatile substances through selecting optimized conditions for injecting samples and preventing thermal decomposition of substances in the course of sample injection. This also ensures reduction in the time required for analyzing multi-component mixtures of substances with a wide range of boiling points of the components thanks to backblowing of part of the heavy (high-boiling) substances not of interest for the purposes of analysis. In addition, the backblow ensures cleaning of the chromatographic column, and especially its inlet portion, from the sample remainders, whereby contamination of the successively analyzed samples of liquid substances is prevented. Another advantage of the proposed gas chromatograph is simplicity and high reliability ensured by the absence of rotary cocks or valves contacting with the material of the sample through its travel path from the injection system to the system for detecting the separated constituents. The proposed chromatograph can be easily ganged up with any known type of automatic sample injecting means using a syringe as the sample carrier. One more advantage of the proposed gas chromatograph resides in that any variations in the operating conditions of the system for injecting the sample and the chromatographic column, including temperature variations and variations in the direction of the flow of carrier gas, fail to influence the operation of the detector, which at any point in time during the chromatographic analysis functions at a constant temperature and flow rate of the carrier gas conveyed therethrough. Other merits of the proposed gas chromatograph include the advantage that the detector is connected to the outlet from the chromatographic column only during conducting the chromatographic analysis of substances, whereas at other points in time that is at intervals between analyses and during bringing the chromatograph to the stable operating conditions, it is disconnected from the chromatographic column and is blown through by the flow of clean carrier gas. This reduces contamination of the inner surfaces of the detector (such as electrodes, electrode insulators, etc.) with vapours of the fixed liquid phase from the chromatographic column, extends the service life of the detector, and provides a stable output signal therefrom, thereby allowing a higher reproducibility of the results of the chromatographic analysis.

What is claimed is:

1. A method of chromatographic analysis of a mixture of liquid subtances in a gas chromatograph comprising a chromatographic column having an inlet portion and an outlet separating portion connected to a detector, which includes a sequence of the following operations:

dividing a flow of carrier gas into at least two parts, particularly first and second parts;

conveying said first part of the flow of carrier gas through said chromatographic column in a direction from the inlet to the outlet;

mixing at the outlet of said chromatographic column of said first part of the flow of carrier gas with the second part of the flow of carrier gas to result in a united flow of carrier gas;

conveying said united flow of carrier gas through said detector;

stabilizing the pressure of said united flow of carrier gas at the inlet of said detector;

introducing a sample of the mixture of substances to be analyzed into said inlet portion of the chromatographic column at a temperature below the boiling point of the substances under analysis;

transferring said substances under analysis to a vaporous state by increasing the temperature in said chromatographic column;

entraining the vapours of said substances under analysis by said first part of the flow of carrier gas through said chromatographic column in a direction from the inlet to the outlet to result in a chromatographic separation of the substances under analysis;

entraining the substances under analysis separated in said chromatographic column by said united flow of carrier gas from the outlet of said chromatographic column to said detector;

detecting said separated substances under analysis in said detector;

conveying said first part of the flow of carrier gas through said chromatographic column in a direction from the outlet to the inlet to result in cleaning of said column from the remainder of the sample material not of interest for the purposes of analysis;

venting to the atmosphere said first part of the flow of carrier gas conveyed through said chromatographic column in a direction from its outlet to the inlet together with the remainder of the sample material not of interest for the purposes of analysis.

2. A method of chromatographic analysis of a mixture of liquid substances with a solvent in a gas chromatograph comprising a chromatographic column having an inlet portion and an outlet separation portion connected to a detector, which includes a sequence of the following operations:

dividing a flow of carrier gas into at least two parts, particularly first and second parts;

conveying said first part of the flow of carrier gas through said chromatographic column in a direction from the inlet to the outlet;

mixing at the outlet of said chromatographic column of said first part of the flow of carrier gas with the second part of the flow of carrier gas to result in a united flow of carrier gas;

conveying said united flow of carrier gas through said detector;

stabilizing the pressure of said united flow of carrier gas at the inlet of said detector;

introducing a sample of the mixture of substances under analysis into said inlet portion of the chromatographic column at a temperature below the boiling point of the substances under analysis and close to the boiling point of the solvent;

conveying said first part of the flow of carrier gas through said chromatographic column in a direction from its outlet to its inlet;

venting to the atmosphere said first part of the flow of carrier gas together with the vapours of said solvent from the inlet of said chromatographic column;

conveying said first part of the flow of carrier gas through said chromatographic column in a direction from its inlet to its outlet;

transferring said substances under analysis to a vaporous state by increasing the temperature in said chromatographic column;

entraining the vapours of said substances under analysis by said first part of the flow of carrier gas through said chromatographic column in a direction from the inlet to the outlet to result in a chromatographic separation of said substances under analysis;

entraining the substances under analysis separated in said chromatographic column by said united flow of carrier gas from the outlet of said chromatographic column to said detector;

detecting said separated substances under analysis in said detector;

conveying said first part of the flow of carrier gas through said chromatographic column in a direction from the outlet of the column to the inlet to result in cleaning said column from the remainder of the sample material not of interest for the purposes of analysis;

venting to the atmosphere of said first part of the flow of carrier gas conveyed through said chromatographic column in a direction from its outlet to the inlet together with the remainder of the sample material not of interest for the purposes of analysis.

3. A method as claimed in claim 2, in which during transferring said substances under analysis to a vaporous state by increasing the temperature of said chromatographic column the temperature of said inlet portion of the column is maintained at a level higher than the temperature of said outlet separating portion of the column.

4. A method of chromatographic analysis of a mixture of liquid substances in a gas chromatograph comprising a chromatographic column having an inlet and an outlet separating portion connected to a detector, which includes a sequence of the following operations:

dividing a flow of carrier gas into at least two parts, particularly first and second parts;

conveying said first part of the flow of carrier gas through said inlet portion of the chromatographic column in a direction from the inlet to the outlet;

dividing at the outlet of said inlet portion of the chromatographic column of said first part of the flow of carrier gas into two parts, particularly third and fourth parts;

venting said third part of the flow of carrier gas to the atmosphere;

conveying said fourth part of the flow of carrier gas through said outlet separating portion of the chromatographic column in a direction from its inlet to the outlet;

mixing at the outlet of said outlet portion of the chromatographic column of said fourth part of the flow of carrier gas with said second part of the flow of carrier gas to result in a united flow of carrier gas;

conveying said united flow of carrier gas through said detector;

stabilizing the pressure of said united flow of carrier gas at the inlet of said detector;

introducing a sample of the mixture of substances to be analyzed to said inlet portion of the chromatographic column at a temperature below the boiling point of the substances under analysis;

transferring said substances under analysis to a vaporous state by increasing the temperature of said inlet portion of the chromatographic column;

entraining the vapours of said substances under analysis by said first part of the flow of carrier gas through said inlet portion of the chromatographic column in a direction from its inlet to the outlet;

venting part of the vapours of said substances under analysis together with said third part of the flow of carrier gas to the atmosphere;

conveying the other part of the vapours of said substances under analysis together with said fourth part of the flow of carrier gas through said outlet separating portion of the chromatographic column to result in chromatographic separation of said substances under analysis;

entraining the substances under analysis separated in said outlet separating portion of said chromatographic column by said united flow of carrier gas to said detector;

detecting said separated substances under analysis in said detector;

conveying said fourth part of the flow of carrier gas through said chromatographic column in a direction from its outlet to the inlet to result in cleaning said chromatographic column from the remainder of the sample material not of interest for the purposes of analysis;

venting to the atmosphere of said fourth part of the flow of carrier gas conveyed through said chromatographic column in a direction from the outlet to the inlet together with the remainder of the sample material not of interest for the purposes of analysis.

5. A gas chromatograph comprising:

a means for introducing a sample of liquid substances to be analyzed by a sample carrier including a chamber for receiving said sample carrier, a passage provided in said chamber wherethrough said sample carrier is received by said chamber;

a first pipe for feeding a carrier gas to said chamber;

a chromatographic column having an inlet portion intended for injecting the sample arranged in said chamber of said means for introducing the sample coaxially with said passage wherethrough the sample carrier is introduced, and an outlet separating portion intended for chromatographic separation of the substances under analysis;

a clearance formed between outer walls of said inlet portion of the column and inner walls of said chamber;

a means for sealing said clearance between the outer walls of said inlet portion of the column and inner walls of said chamber;

a flow restrictor of constant cross-section connected to said outlet separating portion of the column;

a detector intended for detecting separated substances under analysis and arranged at the outlet from siad flow restrictor of constant cross-section;

a means for controlling the flow of carrier gas arranged in said first pipe for feeding the carrier gas;

a second pipe intended for feeding the carrier gas connected to the inlet of said flow restrictor of constant cross-section and to the outlet of said outlet separating portion of the chromatographic column;

a gas pressure regulator arranged in said second pipe for feeding the carrier gas;

a means for sealing said passage provided in said chamber through which passage said sample carrier is received by said chamber, this means having the form of a sealing element connected to said sample carrier.

6. A gas chromatograph as claimed in claim 5, in which said first pipe for feeding the carrier gas is provided with a controllable shut-off valve.

7. A gas chromatograph as claimed in claim 5, in which said means for controlling the flow of carrier gas arranged in said first pipe for feeding the carrier gas has the form of a gas pressure regulator.

8. A gas chromatograph as claimed in claim 5, in which said inlet portion of the chromatographic column is provided with a means for controllably heating and cooling the column.

9. A gas chromatograph comprising:

a means for introducing a sample of liquid substances to be analyzed by a sample carrier including a chamber for receiving said sample carrier; a passage provided in said chamber wherethrough said sample carrier is received by said chamber;

a first pipe for feeding a carrier gas to said chamber;

a chromatographic column having an inlet portion for introducing the sample arranged in said chamber of said means for introducing the sample coaxially with said passage wherethrough the sample carrier is introduced, and an outlet separating portion intended for chromatographic separation of the substances under analysis;

a clearance formed between outer walls of said inlet portion of the column and inner walls of said chamber;

a means for sealing said clearance between the outer walls of said inlet portion of the column and inner walls of said chamber;

a means for dividing the flow of carrier gas into two parts, particularly first and second parts, disposed between said inlet portion of the chromatographic column for receiving the sample and said outlet separating portion of the chromatographic column for carrying out chromatographic separation of the substances under analysis, and having:

a pipe for venting said first part of the flow of carrier gas to the atmosphere, a controllable shut-off valve arranged in said pipe for venting part of the flow of carrier gas to the atmosphere, and a flow restrictor of constant cross-section provided in said pipe for venting part of the flow of carrier gas to the atmosphere;

a means for heating and cooling said inlet portion of the chromatographic column;

a flow restrictor of constant cross-section connected to the outlet from said outlet separating portion of the chromatographic column;

a detector intended for detecting the separated substances under analysis arranged at the outlet of said flow restrictor of constant cross-section;

a means for controlling the flow of carrier gas arranged in said first pipe for conveying the carrier gas;

a second pipe intended for feeding the carrier gas connected to the inlet of said flow restrictor of constant cross-section and to the outlet from said outlet separation portion of the chromatographic column;

a gas pressure regulator arranged in said second pipe for feeding the carrier gas;

a means for sealing said passage provided in said chamber through which passage said sample carrier is received by said chamber, this means having the form of a sealing element connected to said sample carrier.

* * * * *